United States Patent
Workman

(10) Patent No.: US 7,380,455 B2
(45) Date of Patent: Jun. 3, 2008

(54) SYSTEM AND METHOD FOR RESOLVING PHASE AMBIGUITY OF A TRANSDUCER ARRAY TO DETERMINE DIRECTION OF ARRIVAL OF RECEIVED SIGNALS

(75) Inventor: Wayne C. Workman, St. Charles, MO (US)

(73) Assignee: The Boeing Company, Irvine, CA (US)

( * ) Notice: Subject to any disclaimer, the term of this patent is extended or adjusted under 35 U.S.C. 154(b) by 0 days.

(21) Appl. No.: 11/621,529

(22) Filed: Jan. 9, 2007

(65) Prior Publication Data

US 2007/0219742 A1   Sep. 20, 2007

Related U.S. Application Data

(63) Continuation of application No. 10/968,649, filed on Oct. 18, 2004, now Pat. No. 7,201,054.

(51) Int. Cl.
*H01Q 21/06* (2006.01)
*G01N 29/00* (2006.01)

(52) U.S. Cl. .................. 73/602; 342/362; 342/374; 342/424; 342/442; 342/445

(58) Field of Classification Search ............ None
See application file for complete search history.

(56) References Cited

U.S. PATENT DOCUMENTS

| | | | |
|---|---|---|---|
| 5,021,792 A * | 6/1991 | Hwang | 342/357.11 |
| 5,526,001 A * | 6/1996 | Rose et al. | 342/442 |
| 5,574,468 A | 11/1996 | Rose | |
| 5,657,027 A | 8/1997 | Guymon | |
| 5,936,575 A | 8/1999 | Azzarelli et al. | |
| 6,140,963 A | 10/2000 | Azzarelli et al. | |
| 6,195,043 B1 | 2/2001 | Azzarelli et al. | |
| 6,255,991 B1 | 7/2001 | Hedin | |
| 6,583,761 B1 | 6/2003 | Angermeier et al. | |
| 2001/0016505 A1 | 8/2001 | Rexberg et al. | |
| 2003/0020648 A1* | 1/2003 | Fienup | 342/25 |
| 2005/0076717 A1 | 4/2005 | Chevret et al. | |
| 2006/0119503 A1 | 6/2006 | Allen et al. | |

OTHER PUBLICATIONS

Hanson, J.E., "On Resolving Angle Ambiguities on n-Channel Interferometer Systems for Arbitrary Antenna Arrangements in a Plane," Defense Technical Information Center, Oct. 1973, 152 pages, NTIS, U.S. Department of Commerce.

* cited by examiner

*Primary Examiner*—Hezron E. Williams
*Assistant Examiner*—Rose M Miller
(74) *Attorney, Agent, or Firm*—Senniger Powers LLP

(57) ABSTRACT

System and method for resolving phase ambiguities of various transducer arrays, including non-coplanar interferometer antennas on an aircraft skin, in order to determine the direction of arrival of a signal received by the array and emitted by a source remote from the array.

16 Claims, 14 Drawing Sheets

Direction Cosine Sphere

FIG. 7C

Procedure #2
Enter

For each k such that k ≠ i
i is index for 1st element pair
k is index for 2nd element pair

↓

$s_1 = -\pi/2$   $t_1 = -\pi/2$
$s_2 = \pi/2$    $t_2 = \pi/2$
$\Delta s = \pi/20$   $\Delta t = \pi/20$

↓

Set $s = s_1$
$\Delta D = \varepsilon$

↓

For $t = t_1$ to $t_2$ step $\Delta t$
Calculate $D_{ik}$ according to Eq. 17.

↓

$s = s_1$ and $t = t_1$ ? — Yes → $D_0 = D_{ik}$; $t = t + \Delta t$

No ↓

$D_{ik} < D_0$ ? — Yes → (loop back)

No ↓

$t = t - \Delta t$

↓

For $s = s_1$ to $s_2$ step $\Delta s$
Calculate $D_{ik}$ according to Eq. 17.

↓

$D_{ik} < D_0$ ? — No → $D_0 = D_{ik}$; $s = s + \Delta s$

Yes ↓

$D_{ik} < \varepsilon$ ? — No → $\Delta s = \Delta s/2$; $\Delta t = \Delta t/2$ (loop back)

Yes ↓

Store s and t as one pair-wise point of intersection. Record the i and j indices.

↓

Exit

Direction Cosine Sphere

Direction Cosine Sphere

SYSTEM AND METHOD FOR RESOLVING PHASE AMBIGUITY OF A TRANSDUCER ARRAY TO DETERMINE DIRECTION OF ARRIVAL OF RECEIVED SIGNALS

FIELD OF THE INVENTION

The invention generally relates to direction finding systems and methods. In particular, the invention includes a system and method for resolving phase ambiguities of various transducer arrays, including non-coplanar interferometer antennas on an aircraft skin, in order to determine the direction of arrival or angle of arrival of a signal received by the array and emitted by a source remote from the array.

BACKGROUND OF THE INVENTION

The prior art contains several methods of phase ambiguity resolution for interferometric systems consisting of either collinear or non-collinear, coplanar arrangements of transducers, such as antennas. Referring to FIG. 1, in the case of an antenna array, which is sensitive to electromagnetic radiation, antenna elements A1 and A2 of the antenna array are presented with an electromagnetic wave emitted by a remote source. The wave is incident at the "phase centers" of each of the elements A1, A2 of the array from the exact same direction. This direction is referred to as either the direction of arrival (DOA) or the angle of arrival (AOA). Phase ambiguities arise under conditions in which the two antennas are further apart than one half wavelength of the signal carrier wave because practical phase comparators are incapable of discerning a phase angle outside of the range of $\pm \pi$ ($\pm 180°$).

In a treatise published in 1973 by James E. Hanson titled "On Resolving Angle Ambiguities of n-Channel Interferometer Systems for Arbitrary Antenna Arrangements In a Plane" (Defense Technical Information Center Publication Number AD 776-335) addresses ambiguities. In this treatise, Hanson demonstrated how the problem of interferometric phase ambiguity resolution could be easily approached by casting the several differential phase measurements into direction cosine space as a set of equally spaced parallel straight lines; these straight lines arise from recasting the interferometer equation as a linear equation:

$$\psi = \frac{2\pi d_y}{\lambda} \sin\phi \sin\theta + \frac{2\pi d_z}{\lambda} \cos\theta - 2\pi k \quad (1)$$
$$k = 0, \pm 1, \pm 2, \ldots,$$

wherein:
$\Psi$ is the measurable differential phase;
$\lambda$ is the electromagnetic wavelength;
$\phi$ is the azimuth angle;
$\theta$ is the zenith angle;
k is an integer chosen to make $\Psi$ come out in the range of $\pm \pi$; and
$d_y$ and $d_z$ are the y and z components of the inter-element baseline vector.

The meanings of the terms involved in equation (1) are illustrated in FIG. 1. In Hanson's representation $\sin\phi \sin\theta$ and $\cos\theta$ are replaced by Y and Z, respectively, and the new equation is manipulated so that it appears as:

$$Z = -\left(\frac{d_y}{d_z}\right)Y + \frac{\lambda}{2\pi d_z}(\psi + 2\pi k). \quad (2)$$

Equation (2) is the equation of a set of parallel straight lines, one line for each value of the integer k. In addition, Hanson defines a unit circle as:

$$(\sin\phi \sin\theta)^2 + (\cos\theta)^2 = 1. \quad (3)$$

This unit circle describes the limits of visible space in that everywhere on and inside this unit circle $(\sin\phi \sin\theta)^2 + (\cos\theta)^2 \leq 1$. Accordingly, it is referred to as the unit circle of visibility. These sets of parallel lines along with the unit circle centered in direction cosine space are known to those familiar with Hanson's work as Hanson ambiguity diagram and the sets of straight lines are referred to as Hanson ambiguity trajectories. The entire set of trajectories completely describe the ambiguity performance of a linear or a non-linear, coplanar interferometer array (see FIGS. 2 and 2B).

According to Hanson, phase ambiguity resolution is accomplished by finding an arrangement of three or more antennas that create a Hanson ambiguity diagram with but a single point of intersection of the various trajectories, an intersection that is located in direction cosine space at the exact position of the radiating source; for strictly collinear arrays of antennas the single intersection is rather a single straight line. It is also noted that this single point of intersection in direction cosine space leads immediately to the two angles of arrival—$\phi$ the azimuth angle and $\theta$ the zenith angle—so that ambiguity resolution leads immediately to the determination of the angles of arrival (see FIG. 2A).

The differential phase measurements made with practical interferometers come with errors that arise due to systematic as well as thermodynamic perturbations within the array antennas and the receiving network. These errors cause the Hanson trajectories to move or shift randomly at right angles to the directions in which they lay. As a consequence, the single point of intersection in the ideal, no error condition becomes a set of pair-wise trajectory intersections (see FIG. 3). Thus, ambiguity resolution is accomplished by designing the ambiguity resolution computer algorithm so that it can discern a tightly grouped set of pair-wise intersections. Such an approach is described by Azzarelli, et al. in U.S. Pat. No. 6,140,963 but only for non-linear, coplanar arrays.

However, there is a need for a system and an ambiguity resolution method which can deal with non-coplanar arrangements of antenna elements. In addition, there is a need for a system and method which deal with the phase errors that arise due various perturbations and which deal with other than ideal conditions.

SUMMARY OF THE INVENTION

The invention includes a system and method for resolving the angular ambiguities inherent in the differential phase measurements of an interferometric system of non-coplanar antennas. The system and method are also applicable to other transducer systems, such as an underwater sonar system of sonaphonic transducers or a seismic system of acoustic wave transducers or pressure transducers used for oil field exploration. For example, the transducers may be any of the following: antennas, RF sensors, sonaphones, sound sensors, seismic sensors, acoustic wave sensors and/ or pressure sensors. Those skilled in the art will recognize other types of transducer arrays to which the invention is applicable. In general, the invention is applicable to any array having phase ambiguity.

In one embodiment, the invention comprises a system for determining a direction of arrival of a signal (radiation) (radiation) emitted by a source. A first transducer receives the emitted signal (radiation) and provides a first transducer output signal corresponding to the emitted signal received by the first transducer. A second transducer is spaced a distance $D_{12}$ from the first transducer. The second transducer receives the emitted signal and provides a second transducer output signal corresponding to the emitted signal received by the second transducer. A first receiver receives the first transducer output signal and provides a first receiver output signal indicating the phase of the first transducer output signal received by the first transducer. A second receiver receives the second transducer output signal and provides a second receiver output signal indicating the phase of the second transducer output signal received by the second transducer. A processor receives the first receiver output signal and the second receiver output signal, the processor determining a first set of interferometer planes corresponding to a phase difference between the first transducer output signal and the second transducer output signal, the phase difference being a function of the distance $D_{12}$. The processor provides output information corresponding to a direction of arrival of the emitted signal relative to the first and second transducers, wherein the output information is a function of an intersection of the set of interferometer planes with a direction cosine sphere.

In another embodiment, the invention comprises a method for determining a direction of arrival of a signal (radiation) emitted by a source, the method comprising:
receiving the emitted signal with a first transducer and providing a first transducer output signal corresponding to the emitted signal received by the first transducer;
receiving the emitted signal with a second transducer spaced a distance $D_{12}$ from the first transducer and providing a second transducer output signal corresponding to the emitted signal received by the second transducer;
determining a first set of interferometer planes corresponding to a phase difference between the first transducer output signal and the second transducer output signal, the phase difference being a function of the distance $D_{12}$; and
providing output information corresponding to a direction of arrival of the emitted signal relative to the first and second transducers, wherein the output information is a function of an intersection of the set of interferometer planes with a direction cosine sphere.

In another embodiment, a system determines a direction of arrival of a signal (radiation) emitted by a source. Four non-coplanar spaced transducers receive the emitted signal and provide a transducer output signal corresponding to the received, emitted signal. A multi-channel receiver has each channel associated with one of the transducers to receive the associated transducer output signal and each channel provides a digital receiver output signal indicating the phase of the received associated transducer output signal. A digital signal processor receives the digital receiver output signals and processes the received digital receiver output signals by employing a direction finding algorithm to minimize phase ambiguities between the digital receiver output signals to determine a direction of arrival of the emitted signal relative to the transducers.

In another embodiment, the invention comprises a method for determining a direction of arrival of a signal (radiation) emitted by a source, the method comprising:
receiving via four non-coplanar, spaced transducers the emitted signal and providing a transducer output signal corresponding to the received emitted signal from each transducer;
receiving the associated transducer output signal and providing a receiver output signal indicating the phase of the received emitted signal; and
processing the received output signals by employing a direction finding algorithm to minimize phase ambiguities between the received transducer output signals to determine a direction of arrival of the emitted signal relative to the transducers.

In another embodiment, the invention comprises a system for determining a direction of arrival of a signal (radiation) emitted by a source and for resolving front to back phase ambiguity. A plurality of non-collinear, non-coplanar, spaced transducers receives the emitted signal and provide a transducer output signal corresponding to the received emitted signal. A multi-channel receiver has each channel associated with one of the transducers to receive each associated transducer output signal and provides a receiver output signal indicating the phase of the received signal. A processor receives the receiver output signals and processes the received transducer output signals by employing a direction finding algorithm to minimize phase ambiguities between the receiver output signals to determine a first and second direction. The processor determines an amplitude comparison between two of the received transducer output signals of the transducer elements and of the received transducer output signal of another transducer element receiving from a direction substantially opposite to a direction in which of the two transducers receive. The processor selects the first or the second direction as a function of the determined amplitude comparison, the selected direction corresponding to the direction of arrival of the emitted signal relative to the transducers.

In another embodiment, the invention comprises a method for determining a direction of arrival of a signal (radiation) emitted by a source and for resolving front to back phase ambiguity, the method comprising:
receiving the emitted signal via a plurality of non-collinear, non-coplanar, spaced transducers, and providing a transducer output signal corresponding to the received emitted signal from each transducer;
receiving each associated transducer output signal and providing a receiver output signal indicating the phase of the received emitted signal;
processing the received transducer output signals by employing a direction finding algorithm to minimize phase ambiguities between the received transducer output signals to determine a first and second direction;
determining an amplitude comparison between the received transducer output signals of two of the transducer elements and the received transducer output signal of another transducer element receiving from a direction substantially opposite to a direction in which of the two transducers receive;
selecting the first or the second direction as a function of the determined amplitude comparison, the selected direction corresponding to the direction of arrival of the emitted signal relative to the transducers.

Other objects and features will be in part apparent and in part pointed out hereinafter.

BRIEF DESCRIPTION OF THE DRAWINGS

Figure 1:
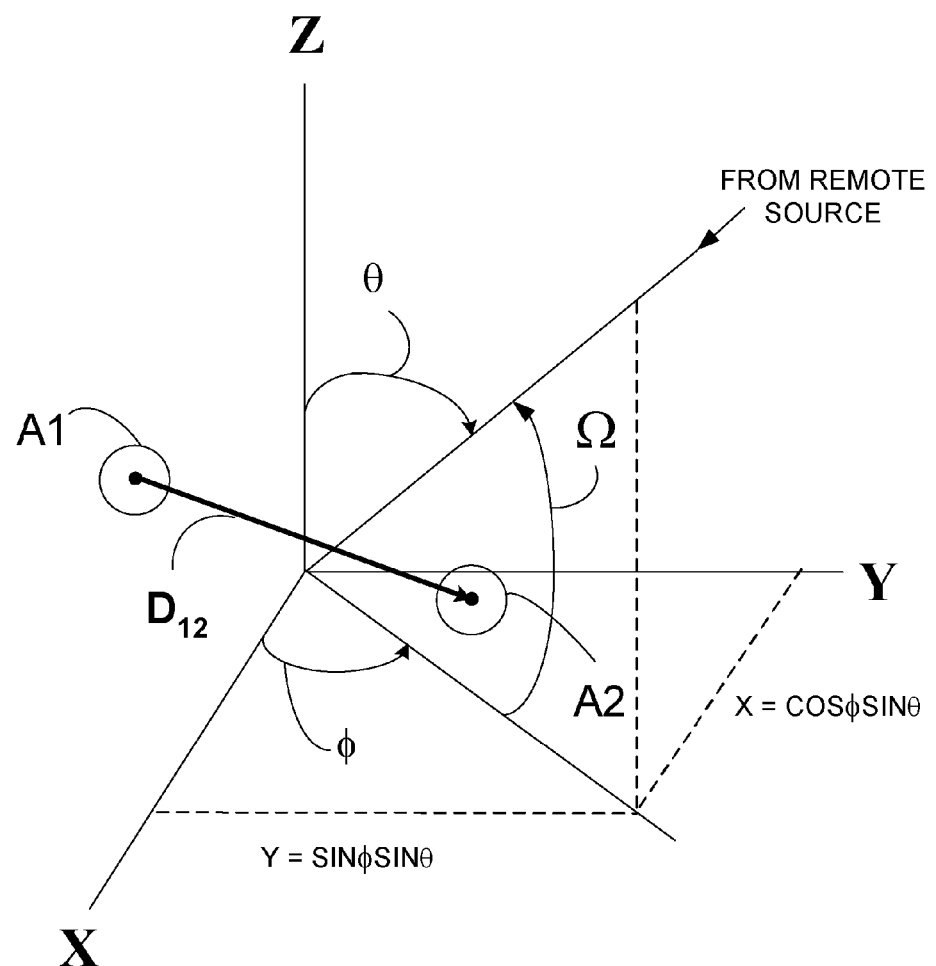

Having thus described the invention in general terms, reference will now be made to the accompanying drawings wherein:

FIG. 1 is an illustration of the geometric relationship of the interferometer equation (1) between two antennas, A1 and A2, located arbitrarily in the Y-Z plane and separated by a distance $D_{12}$.

Figure 2A:
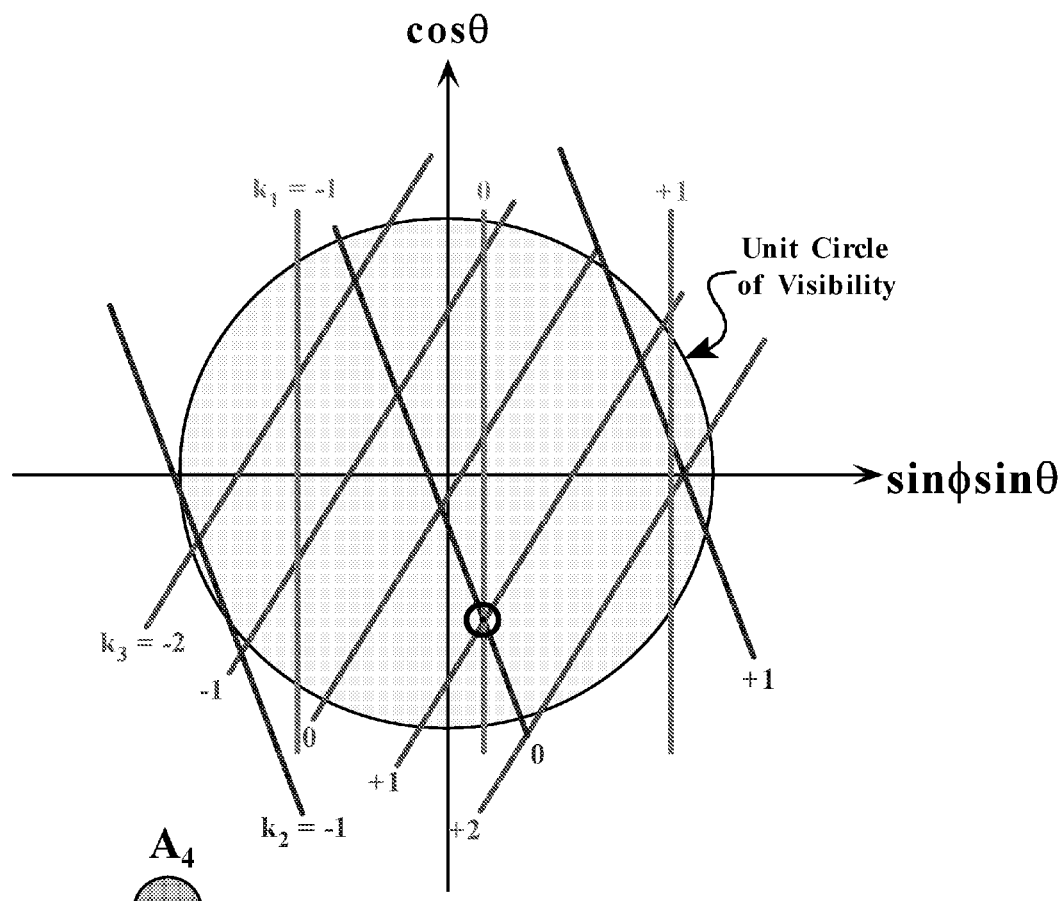
Figure 2B:
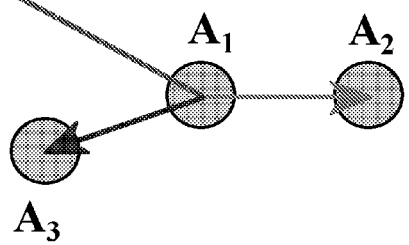

FIG. 2A illustrates a Hanson ambiguity diagram for a four element interferometer array as illustrated in FIG. 2B.

Figure 3:
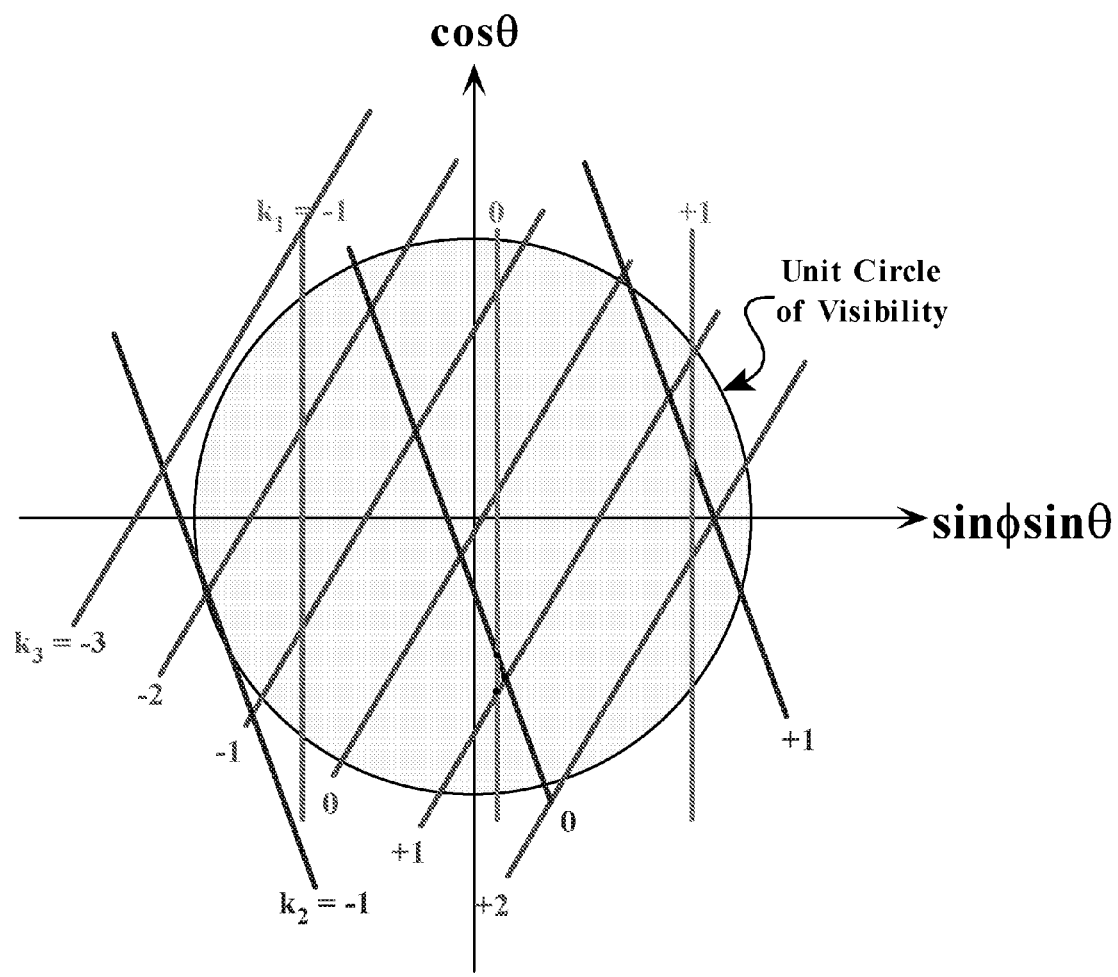

FIG. 3 is diagram illustrating an ambiguity for the four element interferometer array of FIG. 2 and further illustrating the effects of phase errors on the ambiguity trajectories.

Figure 4:
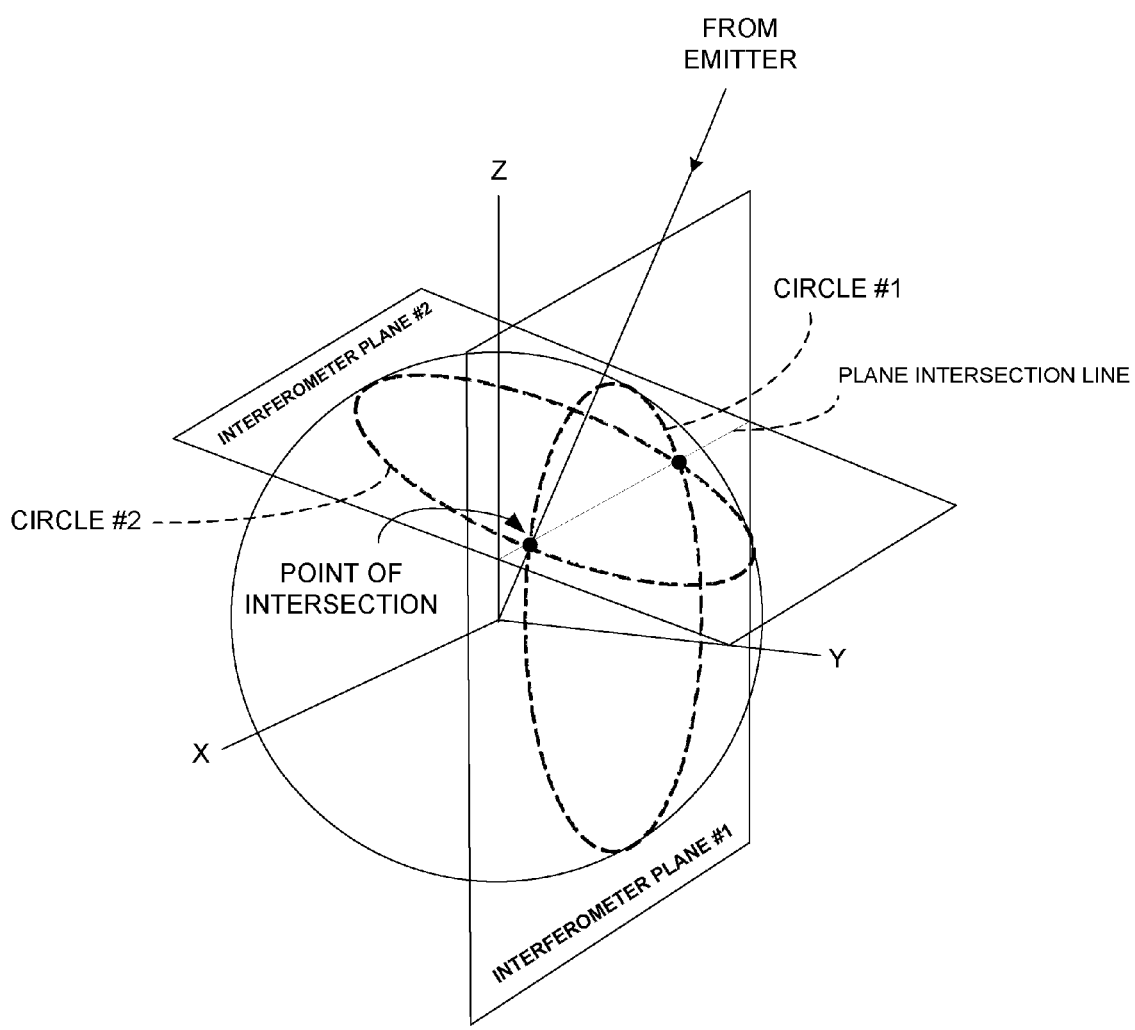

FIG. 4 is an illustration of the relationship between the direction cosine sphere and the interferometer planes showing in dashed lines the two circles of intersection of the sphere and the planes and showing the point of intersection of the two circles of intersection, according to the invention.

Figure 5:
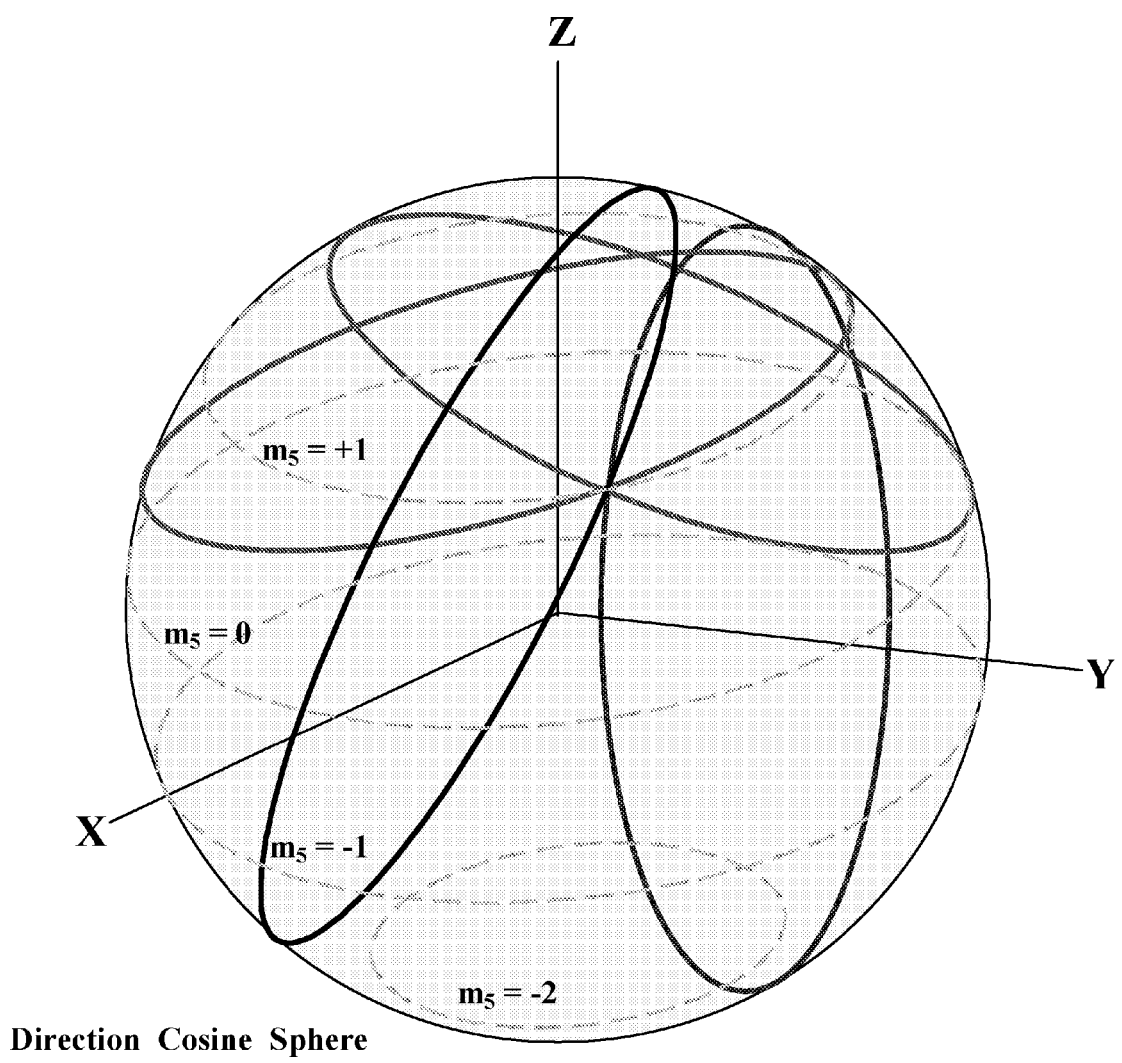

FIG. 5 is an illustration of a direction cosine sphere with ambiguity circles; four of the ambiguity circles are intersect at a single point, while the fifth circle is represented as four separate dashed line circles, each with a different ambiguity integer.

Figure 6:
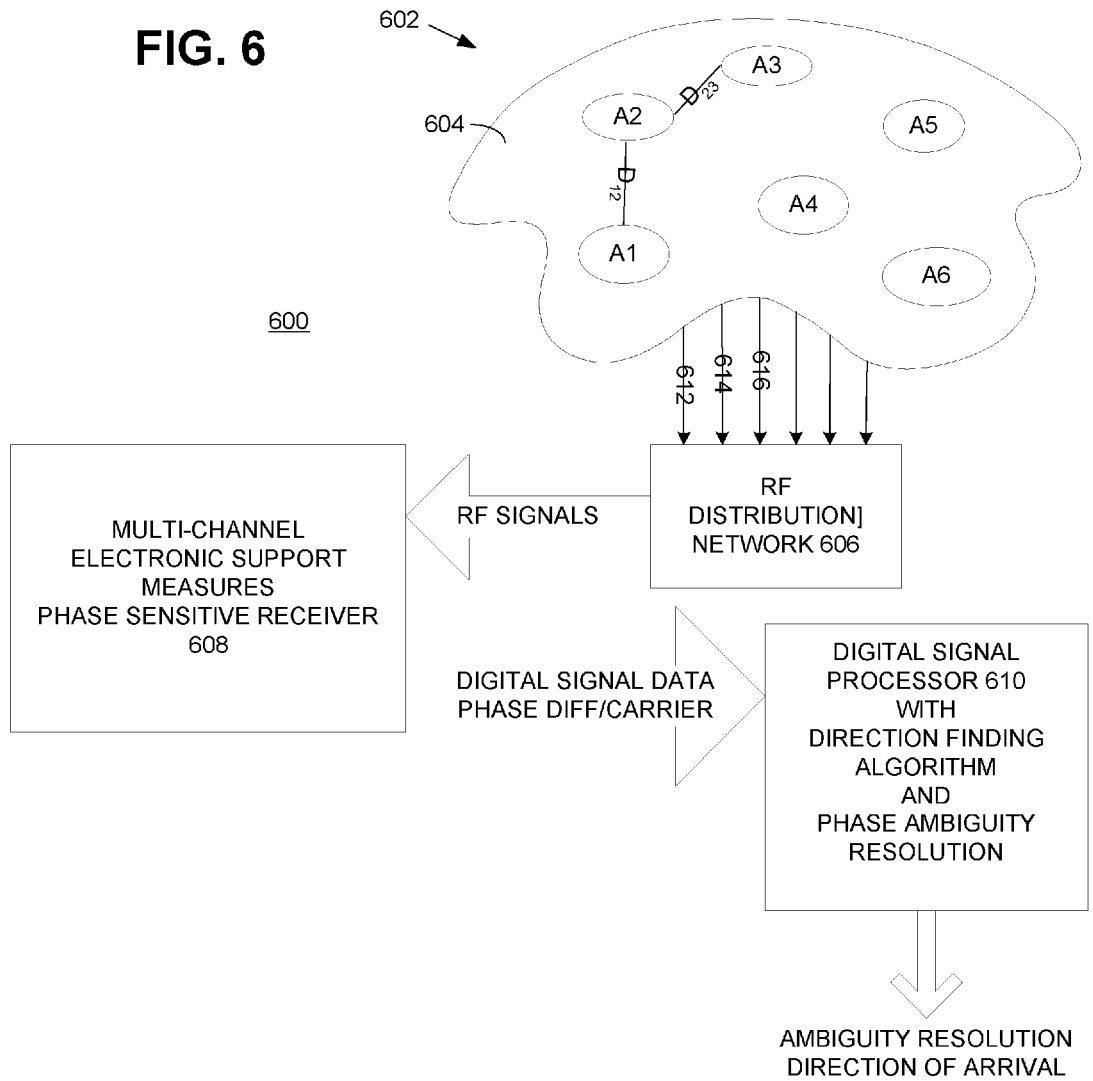

FIG. 6 is an illustration, partially in block diagram form, of a system of the invention including six surface embedded antenna elements A1-A6 on a curved surface.

FIGS. 7A-7D illustrate a procedure according to the invention for determining a value of the parameter t that minimizes the value of $D_{ij}$.

Figure 8:
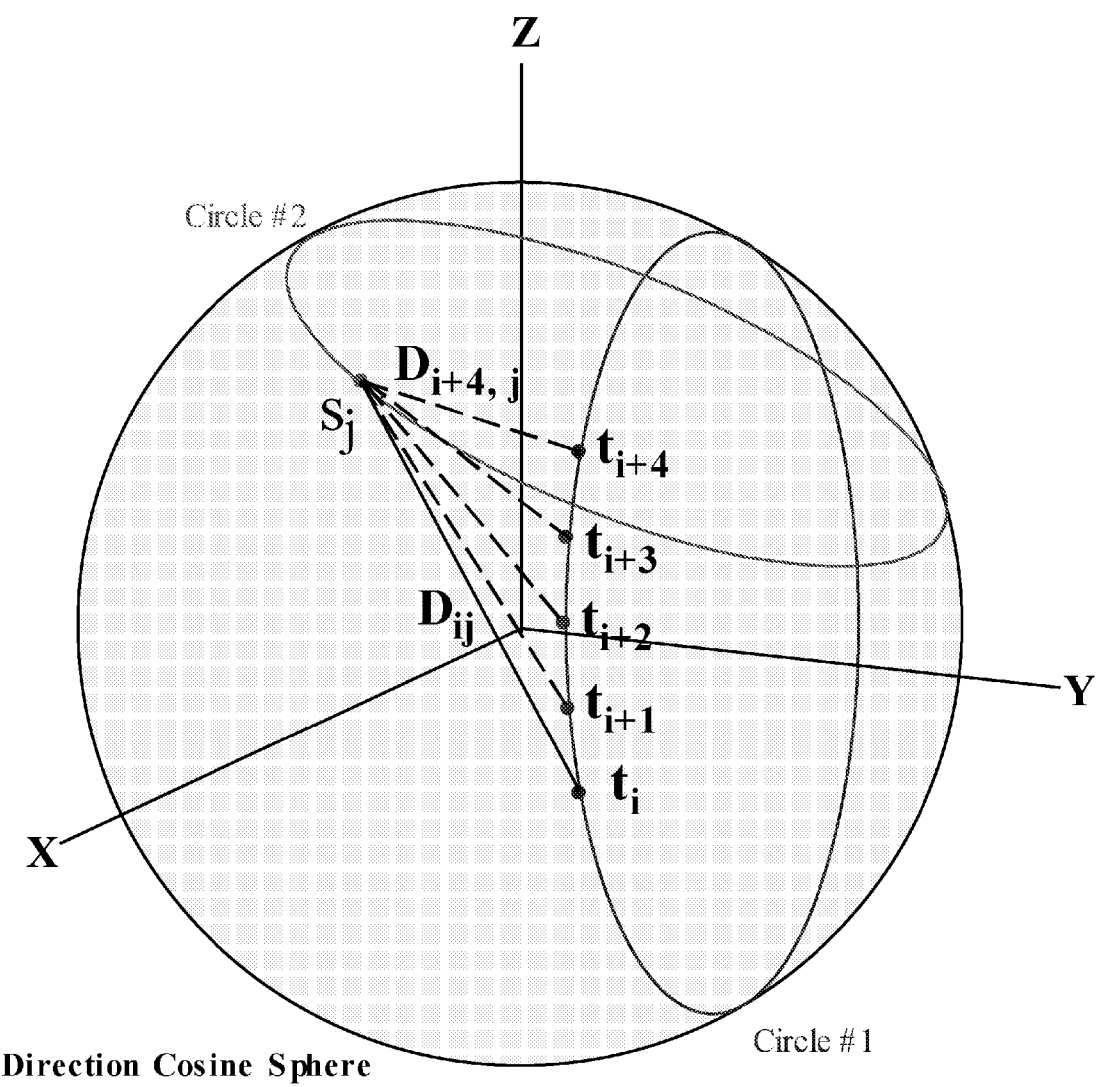
Figure 9:
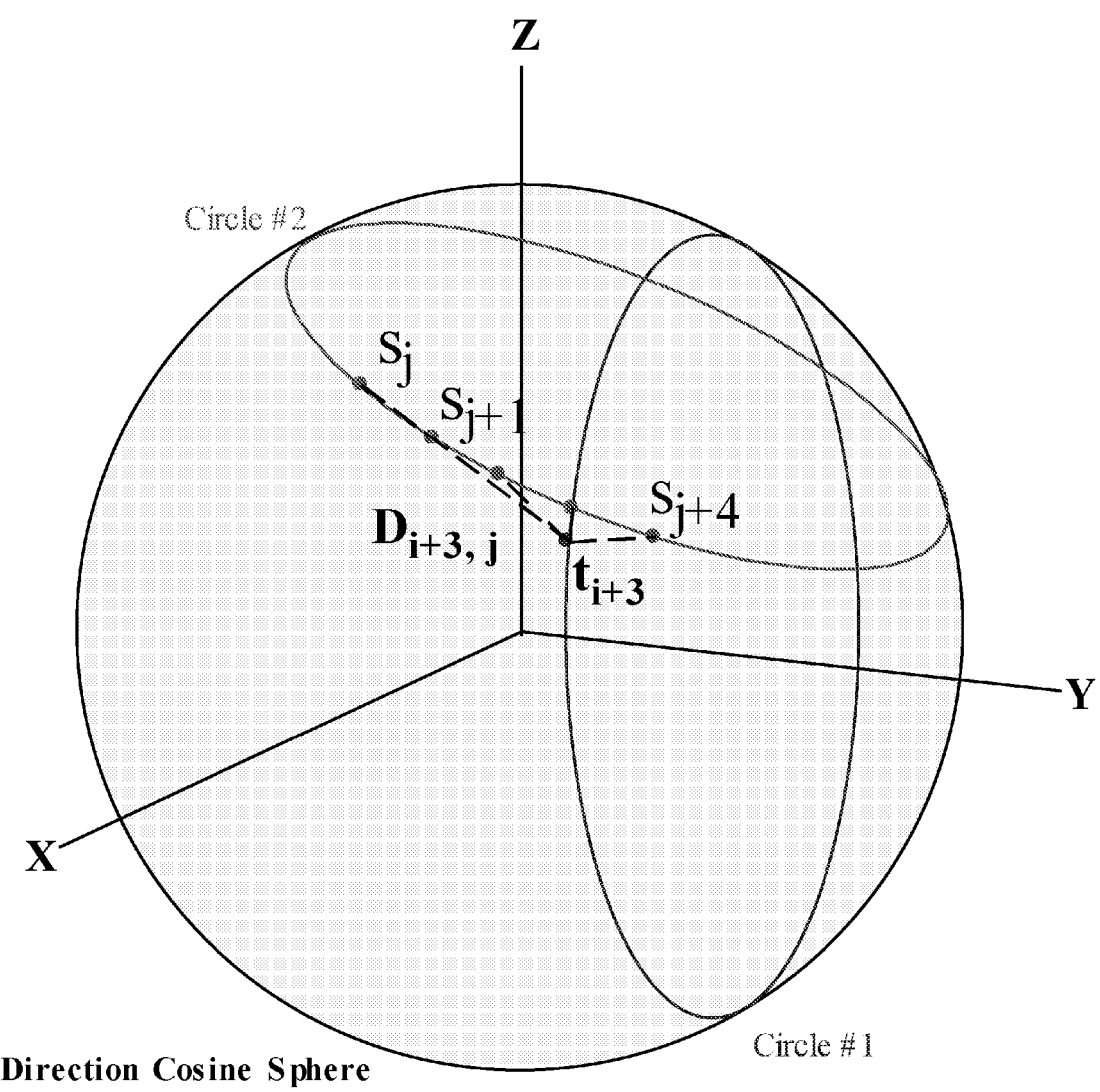

FIGS. 8 and 9 illustrate the process of determining the common point of intersection.

Figure 10:
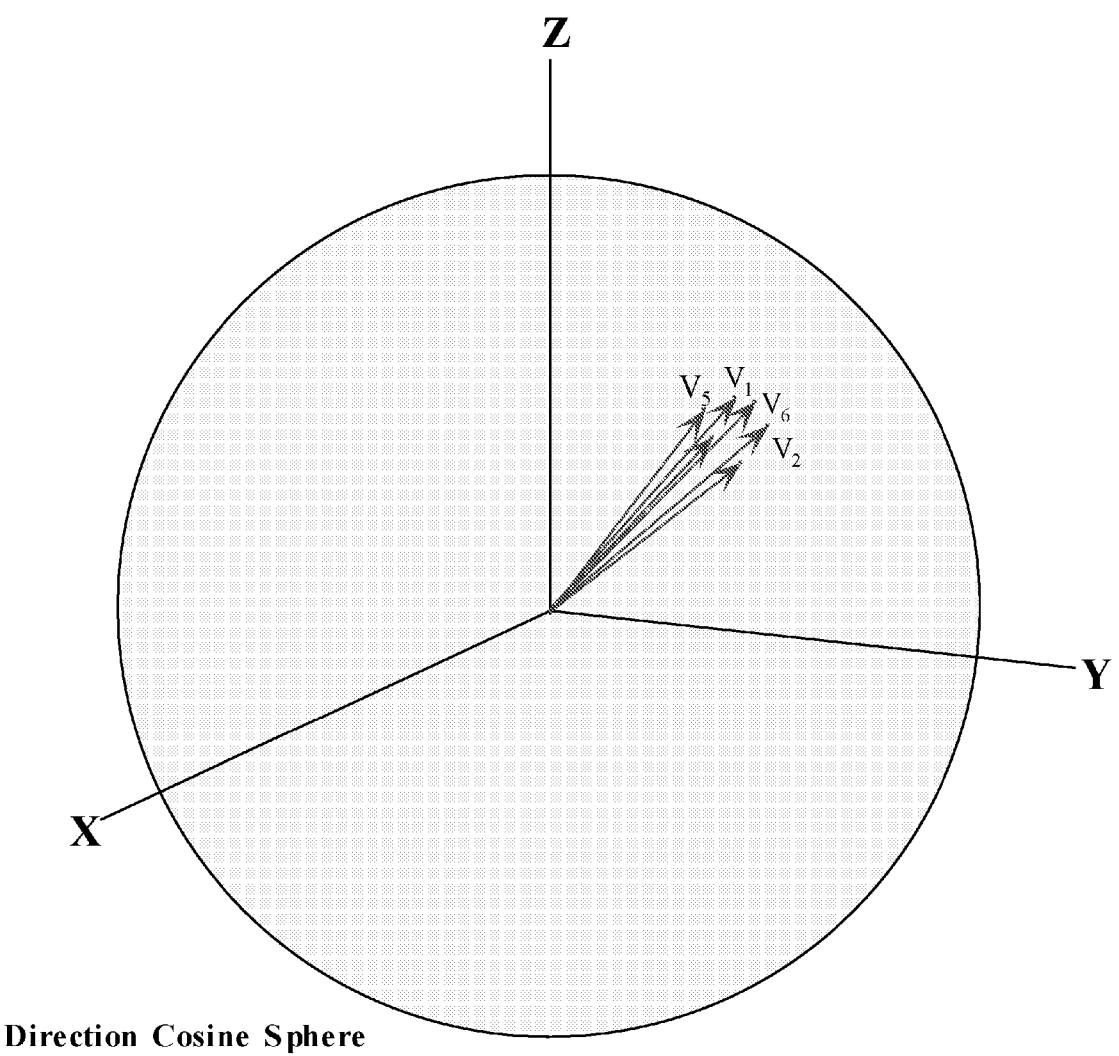
Figure 11:
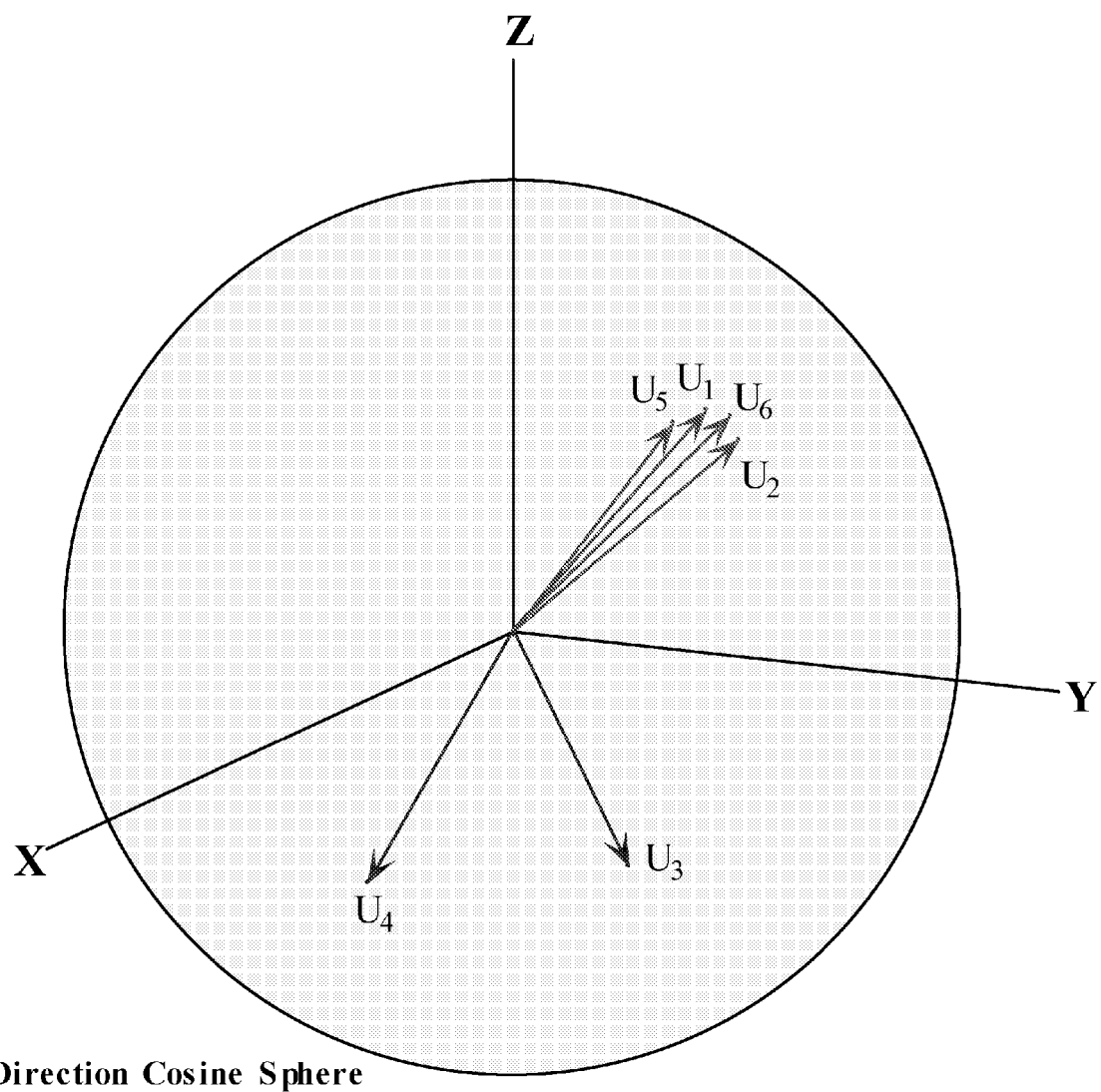

FIGS. 10 and 11 illustrate the direction vectors from the process of determining the common point of intersection.

Corresponding reference characters indicate corresponding parts throughout the drawings.

DETAILED DESCRIPTION OF THE PREFERRED EMBODIMENT

In general, a collection of a plurality of antennas or transducers within a single system is commonly referred to as an array. In this description a practical interferometric system shall comprise of such an array of antennas or transducers, each element of which is connected to a channel of a multichannel receiver. The connection may be either directly to a single channel of a multiple channel receiving network or indirectly through a multiplexing switch selection network sharing one channel of the receiving network amongst two or more antennas. Additionally, such systems are also equipped with a processor for executing certain algorithms among which are algorithms specifically designed to carry out the phase ambiguity resolution calculations.

It is contemplated that the system and method may be any array of transducers. For clarity and simplicity, the system and method of the invention will be described below in the context of an antenna array having two antenna elements. Those skilled in the art will recognize various transducer arrays, including but not limited to light, sound, radio frequency or other radiation transducers, which may be embodied in the system and/or method of the invention. Those skilled in the art will also recognize that such arrays may comprise more than two transducers.

The present invention deals with non-coplanar arrangements of antennas, although it will work equally well for co-planar arrangements. FIG. 4 is based on a pair antennas arbitrarily arranged in a three dimensional coordinate system. Unlike the antenna pair in FIG. 1, in this arrangement the inter-baseline vector has an x-component as well as a y- and a z-component. This x-component alters the interferometer equation from that of Eq. 1 so that the new form appears as $$\psi = \frac{2\pi d_x}{\lambda}\cos\phi\sin\theta + \frac{2\pi d_y}{\lambda}\sin\phi\sin\theta + \frac{2\pi d_z}{\lambda}\cos\theta - 2\pi m \quad (4)$$

$$m = 0, \pm 1, \pm 2, \ldots.$$

Replacing $\cos\phi\sin\theta$ with X, $\sin\phi\sin\theta$ with Y, and $\cos\theta$ with Z, this last equation can be manipulated into the following form:

$$\frac{\lambda}{d}\left(\frac{\psi}{2\pi} + m\right) = \left(\frac{d_x}{d}\right)X + \left(\frac{d_y}{d}\right)Y + \left(\frac{d_z}{d}\right)Z. \quad (5)$$

wherein $d = \sqrt{d_x^2 + d_y^2 + d_z^2}$. This is the equation of a set of parallel planes, one plane for each value of the ambiguity integer m; these planes as well as whole sets of these planes are referred to as interferometer planes. The normal to the surfaces of these interferometer planes is given by $$n = \frac{d_x}{d}i + \frac{d_y}{d}j + \frac{d_z}{d}k. \quad (6)$$

The unit vector extending from the origin of configuration space coordinate system in the direction of the distant emitter is given by the expression $$\hat{r} = \cos\phi\sin\theta \hat{i} + \sin\phi\sin\theta \hat{j} + \cos\theta \hat{k}. \quad (7)$$

Equation (7) in light of the substitutions above can be recast into the direction cosine space expression:

$$\hat{r} = X\hat{i} + Y\hat{j} + Z\hat{k}. \quad (8)$$

This unit vector also defines a sphere in direction cosine space, the radius of which is exactly 1:

$$X^2 + Y^2 + Z^2 = 1. \quad (9)$$

This sphere is referred to as the direction cosine sphere and the planes defined by Eq. 5 will intersect this sphere in a set of curves and the distant emitter must lay along a line in direction cosine space that begins at the origin and extends outward through the surface of the sphere along one of these curves of intersection. As shown in FIG. 4 these curves of intersection of a plane with a sphere are always either a circle or a mere point, a point being a degenerate circle the radius of which is exactly zero. This circular curve of intersection is referred to as an ambiguity circle, e.g., circle #1 and circle #2.

The distance, $d_n$, between the origin of the direction cosine space coordinate system and the plane defined by Eq. 5 along the normal vector defined in Eq. 6 is given by $$d_n = \frac{\lambda}{d}\left(\frac{\psi}{2\pi} + m\right). \quad (10)$$

The allowed values of the ambiguity integer m are those for which $d_n$ falls within $-1$ and $+1$. For if m were chosen so as to make $d_n$ greater than 1 (or less than $-1$), the corresponding interferometer plane would not then intersect with the direction cosine sphere. While such interferometer planes exist mathematically, they are said to reside in invisible space. It is apparent from this last equation that the ambiguity integer m is bounded within the range $$m = \pm INT\left[\frac{d}{\lambda} + \frac{1}{2}\right].\quad(11)$$

Reference is made again to FIG. 4 where two interferometer planes are illustrated intersecting with the direction cosine sphere each forming a separate ambiguity circle, e.g., circle #1 and circle #2. These two circles are created by an interferometer consisting of three antennas. Although not shown in FIG. 4, each pair of antennas, if the inter-element distance is great enough, will give rise to several such ambiguity circles each, and some of the ambiguity circles of one pair will undoubtedly intersect with some of the ambiguity circles of the other pair, creating multiple points of intersection or angular ambiguities. A practical interferometer will include four or more antennas that can be arranged so that only a single ambiguity circle from each set will intersect at a single common point.

Reference is made to FIG. 5 where the interferometer system consists of six antennas creating five sets of ambiguity circles. In this illustration a common point of intersection has been found for the first four sets of ambiguity circles and the phase ambiguity resolution algorithm is testing the four circles of the fifth set to see which passes through (or closest to) the previously determined common point of intersection for the first four sets.

When the antennas are arrayed in a non-coplanar manner, there is but one common point of intersection for the proper ambiguity circles of all of the sets. This point is in effect "in front" of the interferometer array antennas in that this point and the emitter both reside in the same forward hemisphere where X is positive. When the antennas are arranged as a coplanar array, there are two points of intersection of the proper ambiguity circles of all of the sets, one point in the forward hemisphere and yet a second in the rear hemisphere. The prior art contains several method for resolving this "front-back" ambiguity customarily involving a preferentially rearward facing antenna. In this way, the signal (radiation) amplitude received by this rearward facing antenna is compared with the signal (radiation) amplitude received by one of the "forward facing" interferometer antennas. If the signal amplitude received by the rearward facing antenna is greater than the signal amplitude received by the interferometer antenna, the emitter is "declared to be behind the interferometer and all direction finding processing halted for that signal. In the remainder of this application the discussion will proceed as if there is but a single point of intersection for two ambiguity circles, when in fact there are always two such points—one in the forward hemisphere and one in the rear hemisphere. It is to be understood that the algorithms being discussed have the primary objective of finding only the point of intersection in the forward hemisphere.

FIG. 6 illustrates the preferred embodiment of an interferometer system 600 according to the invention including a non-coplanar antenna array 602 on an aircraft skin 604. In this FIG. 6, the interferometer array 602 is shown with a total of six antennas A1-A6, all laying on a common complex surface which is assumed for exemplary purposes only to be an aircraft skin 604. As shown in FIG. 6, the RF signal paths out of these antennas go through an RF distribution network 606 where the signals from the antennas A1-A6 are shared amongst the channels of a phase sensitive, multi-channel electronic support measures receiver 608. Optionally, the number of receiver channels may and (and is assumed to be) fewer than the number of antennas. Following the extraction of incident signal's characteristics (RF frequency, pulse width, signal amplitude and channel-channel phase differences) by the electronic support measures receiver 608, digital representations of these characteristics are past to a digital signal processor 610 where, among other processes, ambiguity resolution and angle of arrival processing take place.

In one embodiment, the digital signal processor 610 receives digital receiver output signals indicating the phase of the signals received by the antennas and processes the received digital receiver output signals by employing a direction finding algorithm to minimize phase ambiguities between the digital receiver output signals to determine a direction of arrival of the emitted signal relative to the antennas.

As a result, system 600 determines a direction of arrival of a signal (radiation) emitted by a source which is remote from array 602. The array 600 includes at least a first antenna A1 for receiving the emitted signal and for providing a first antenna output signal 612 corresponding to the emitted signal received by the first antenna. The array also includes at least a second antenna A2 spaced a distance $D_{12}$ from the first antenna A1. The second antenna A2 also receives the emitted signal and provides a second antenna output signal 614 corresponding to the emitted signal received by the second antenna. The multi-channel receiver 608 includes a first receiver for receiving the first antenna output signal 612 and for providing a first receiver output signal (e.g., digital signal data) indicating the phase of the first antenna output signal received by the first antenna (and possibly indicating the carrier). The multi-channel receiver 608 includes a second receiver for receiving the second antenna output signal 614 and for providing a second receiver output signal (e.g., digital signal data) indicating the phase of the second antenna output signal received by the second antenna (and possibly indicating the carrier). The processor 610 receives the first receiver output signal and the second receiver output signal and determines a first set of interferometer planes corresponding to a phase difference between the first antenna output signal and the second antenna output signal. As explained herein, the phase difference is a function of the distance $D_{12}$. The processor 610 provides output information corresponding to a direction of arrival of the emitted signal relative to the first and second antennas. As explained herein, the output information is a function of an intersection of the set of interferometer planes with a direction cosine sphere.

In one embodiment, the first receiver output signal has a phase corresponding to the phase of the signal received by the first antenna and the second receiver output signal has a phase corresponding to the phase of the signal received by the second antenna.

In one embodiment as described herein, the system resolves front to back phase ambiguity. The processor 610 processes the received antenna output signals by employing a direction finding algorithm to minimize phase ambiguities between the receiver output signals to determine a first and second direction. The processor determines an amplitude comparison between two of the received antenna output signals of the antenna elements and of the received antenna output signal of another antenna element (not shown) receiving from a direction substantially opposite to a direction in which of the two antennas receive. The processor selects the first or the second direction as a function of the determined amplitude comparison, the selected direction corresponding to the direction of arrival of the emitted signal relative to the first and second antennas.

Optionally, the system 600 may include additional antennas such as a third antenna A3 receiving the emitted signal and providing a third antenna output signal corresponding to the emitted signal received by the third antenna A3. The third antenna is spaced a distance $D_{23}$ from the second antenna A2. The receiver 608 includes a third receiver for receiving the third antenna output signal and providing a third receiver output signal indicating the phase of the third antenna output signal received by the third antenna A3. In this optional embodiment, the processor receives the third receiver output signal and determines a second set of interferometer planes corresponding to a phase difference between the second antenna output signal and the third antenna output signal. As described herein, the phase difference is a function of the distance $D_{23}$. The processor provides output information corresponding to a direction of arrival of the emitted signal relative to the first, second and third antennas A1-A3. As described herein, the output information is a function of an intersection of the second set of interferometer planes with a second direction cosine sphere.

The invention also includes the method for determining the direction of arrival of the signal (radiation) emitted by a source. The method comprises:

receiving the emitted signal with the first antenna A1;
receiving the emitted signal with the second antenna A2;
  determining a first set of interferometer planes corresponding to a phase difference between the emitted signals; and
providing output information corresponding to a direction of arrival of the emitted signal relative to the first and second antennas, wherein the output information is a function of an intersection of the set of interferometer planes with a direction cosine sphere.

One embodiment includes a method for determining a direction of arrival of a signal (radiation) emitted by a source and for resolving front to back phase ambiguity, wherein the method comprises:

processing the received antenna output signals by employing a direction finding algorithm to minimize phase ambiguities between the received antenna output signals to determine a first and second direction;
determining an amplitude comparison between the received antenna output signals of two of the antenna elements and the received antenna output signal of another antenna element receiving from a direction substantially opposite to a direction in which of the two antennas receive; and
selecting the first or the second direction as a function of the determined amplitude comparison, wherein the selected direction corresponds to the direction of arrival of the emitted signal relative to the antennas.

Another embodiment includes an iterative method of arranging a plurality of antennas (particularly non-collinear, non-coplanar spaced antennas) having phase errors in order to use the antennas to determine a direction of arrival of a signal (radiation) emitted by a source. In this iterative method, a set of circle pair intersections for each pair of the plurality of antennas is determined. The relative position of the antennas is then modified (e.g., by modifying the spacing) and a modified set of circle pair intersections for each pair of the plurality of antennas after modifying the position is determined. The set of circle pair intersections is compared with the modified set of circle pair intersections to determine the more tightly grouped set of circle pair intersections. The antennas are arranged according the position which corresponds to the more tightly grouped set of circle pair intersections. The resulting antenna array also embodies the invention. The interactive method may instead include and may also include modifying the preset number of the antennas (e.g., adding or removing antennas from the array) and determining a modified set of circle pair intersections for each pair of the plurality of antennas after modifying the preset number. The set of circle pair intersections before modifying is compared with the modified set of circle pair intersections to determine the more tightly grouped set of circle pair intersections. The array is then assembled with a number of antennas which number which corresponds to the more tightly grouped set of circle pair intersections. The resulting antenna array also embodies the invention.

The "Best" Set of Pair-Wise Intersections

In the present case, the objective of the ambiguity resolution algorithm is to determine the common point of intersection of the various ambiguity circles. An actual algorithm will involve a set of nested loops each of which iterates through the allowed values of the ambiguity integer associated with each pair of array antennas. In this manner, every combination of the ambiguity circles of all the several sets are examined until the "best" set is discovered by comparison.

In practical interferometers thermal noise disturbances and other sources of phase error quite often prevent the proper set of ambiguity circles from all crossing at a single common point. In these cases then, some criteria is established, such as the most tightly grouped set of pair-wise points of intersection, which when found is declared to be the "best" set of pair-wise intersections from which a common point can be derived. The following is the description of the preferred algorithm designed to find the most tightly grouped set of ambiguity circle intersection points. It is pointed out here that the single most important aspect of this algorithm is the determination of the point of intersection of two ambiguity circles from separate sets of interferometer planes. The following description explains some embodiments as to how this objective is accomplished.

The first step is to determine the radius of the $j^{th}$ ambiguity circle of the $i^{th}$ set of interferometer planes. (The algorithm described herein below is illustrated by the flow charts contained in FIGS. 11 through 14.) By the Pythagorean theorem if the normal distance from the surface of the interferometer plane back to the origin is given by Equation 10, then the radius of the $j^{th}$ ambiguity circle is given by $$R_{ij} = \sqrt{1 - d_{ni}} = \sqrt{1 - \left\{\frac{\lambda}{d_{ni}}\left(\frac{\psi_i}{2\pi} + m_{ij}\right)\right\}^2}. \tag{12}$$

The next step is to recognize that the normal vector to the $i^{th}$ interferometer plane provides the basis for defining a coordinate system in which the ambiguity circles of the $i^{th}$ interferometer planes are most simply defined. This normal vector is given in Eq. 6 and is repeated here for completeness:

$$n = \frac{d_x}{d}i + \frac{d_y}{d}j + \frac{d_z}{d}k. \qquad (6)$$

Let this vector be the unit vector in the direction of the z-axis in this new coordinate system—referred to hereafter as the primed coordinate system. Form the unit vector in the direction of y' by setting the x-axis component equal to zero and interchanging the y and the z components and negating the new y' component:

$$z' = \frac{d_x}{d}i + \frac{d_y}{d}j + \frac{d_z}{d}k, \qquad (13a)$$

and $$y' = -\frac{d_z}{d'}j + \frac{d_y}{d'}k \qquad (13b)$$

wherein $$d' = \sqrt{d_y + d_z}.$$

The vector cross product of these two vectors gives the unit vector aligned with the x'-axis.

$$x' = y' \times z' = \frac{1}{dd'}\{-(d_z^2 + d_y^2)\hat{i} + (d_x d_y)\hat{j} + (d_x d_z)\hat{k}\}. \qquad (13c)$$

These three unit vectors form a basis set for a Cartesian coordinate system that is at once lined up with the normal vector to the interferometer plane with its x'-y' coordinate axes residing in the interferometer plane. Vector transformations from the primed to the unprimed coordinate systems can be accomplished using the 3-by-3 matrix $$T = \frac{1}{dd'}\begin{pmatrix} -(d_y^2 + d_z^2) & 0 & d'd_x \\ d_x d_y & -dd_z & d' \cdot d_y \\ d_y d_z & dd_y & d'd_z \end{pmatrix} \qquad (14)$$

Now, in this new primed coordinate system the parametric equation of the circle of intersection of $i^{th}$ interferometer plane with the direction cosine sphere is easily seen to be $$r_i(t) = [R_i \cos(t)]\hat{i}' + [R_i \sin(t)]\hat{j}' + \frac{\lambda}{d_{ni}}\left(\frac{\Psi_i}{2\pi} + m_{ij}\right)\hat{k}'. \qquad (15)$$

This parametric form of the ambiguity circle is transformed to the unprimed coordinate system using the transformation matrix of Eq. 13.

The ambiguity circles of a second or subsequent interferometer plane results in a similar equation within a double primed coordinate system:

$$r_k(s) = [R_k \cos(s)]\hat{i}'' + [R_k \sin(s)]\hat{j}'' + \frac{\lambda}{d_{nk}}\left(\frac{\Psi_n}{2\pi} + m_{kj}\right)\hat{k}''. \qquad (16)$$

and again a similar transformation matrix as in equation 13 transforms this vector equation from the doubly primed coordinate system to the unprimed coordinate system, allowing the two parametric equations can be calculated in the same coordinate system.

Figure 7A:
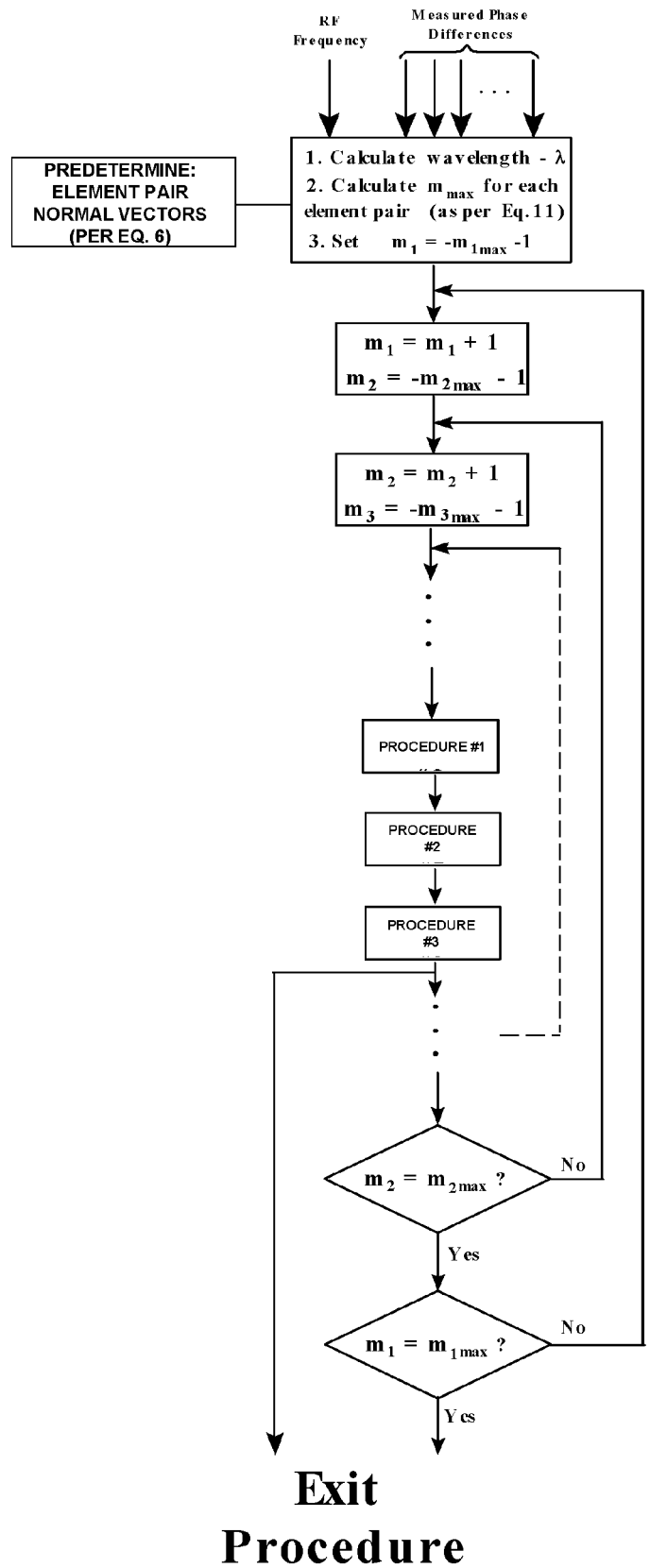
Figure 7B:
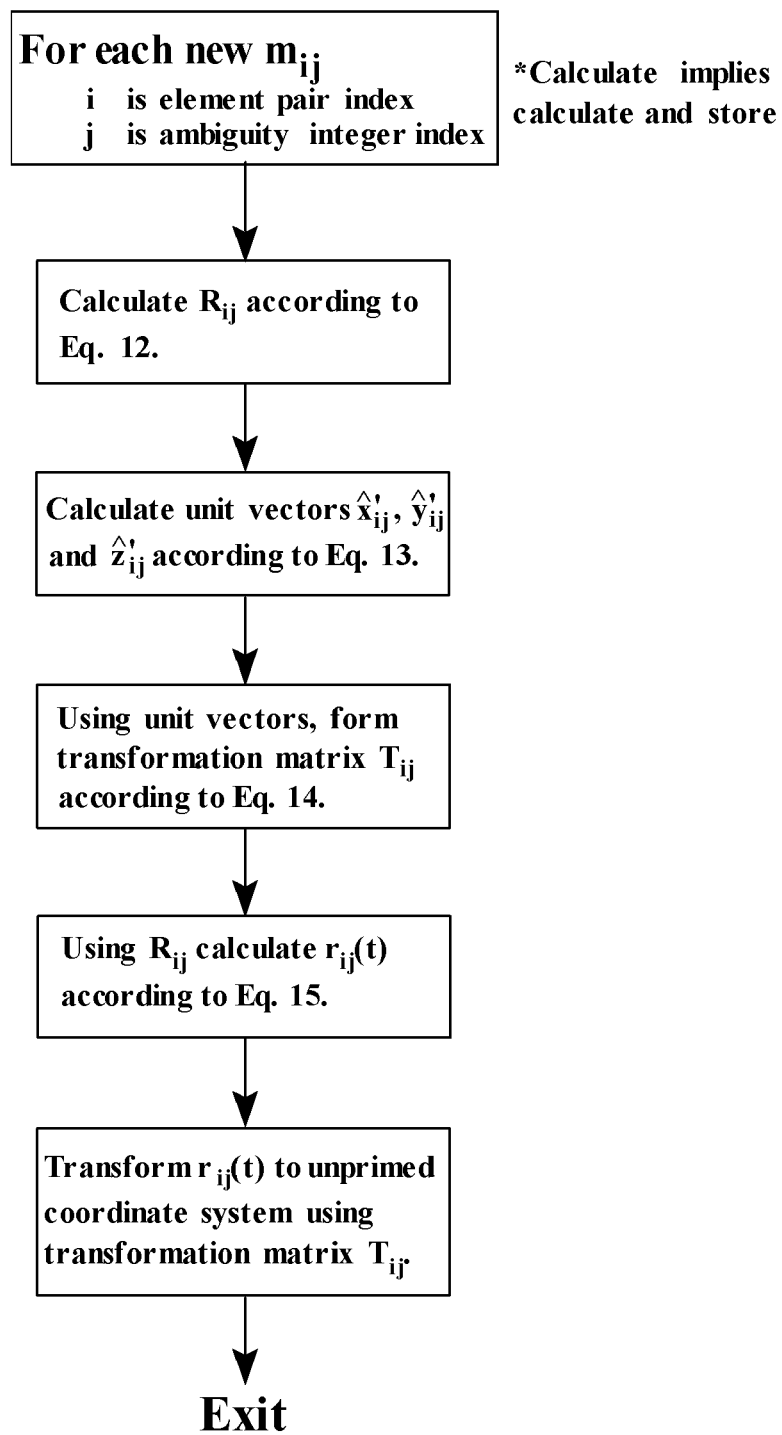
Figure 7D:
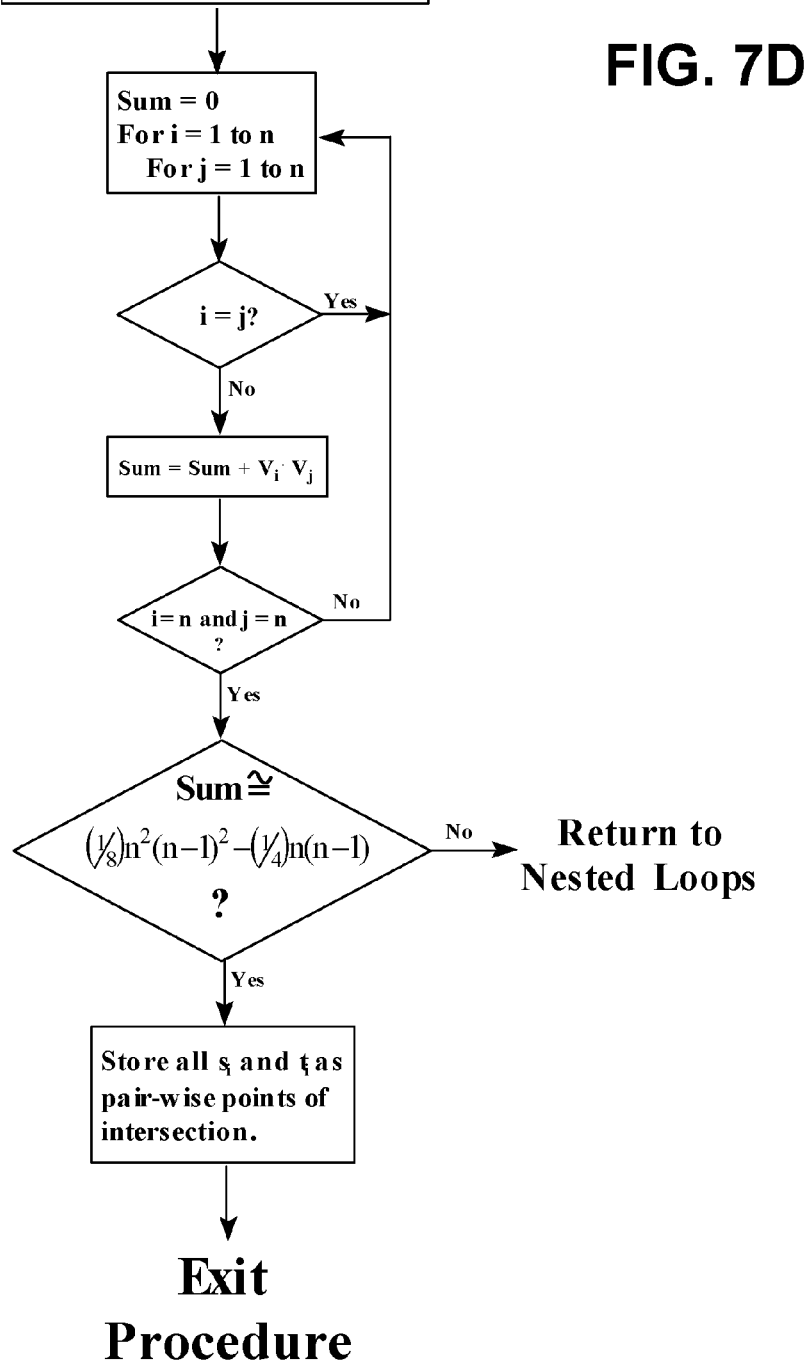

To find the common point between the two ambiguity circles, the parameter s is held constant at some convenient value while the parameter t is varied in small increments over a range of values that keep the x-component of $r_i$ positive, thus assuring that the common point of intersection, were it to be found, would be in the forward hemisphere. The search procedure is illustrated in FIGS. 7A-7D. Initially, the process as shown in FIG. 7B looks for a value of the parameter t that minimizes the value of $D_{ij}$.

$$D_{ij} = \sqrt{\{x(t_i) - x(s_j)\}^2 + \{y(t_i) - y(s_j)\}^2 + \{z(t_i) - z(s_j)\}^2}. \qquad (17)$$

At this point reference is made to FIG. 8, where as illustrated $t_{i+3}$ is the point that minimizes $D_{ij}$. The search over t is halted at this point and the value of the parameter t retained at this value.

Next, the process of the algorithm as shown in FIG. 7C conducts a search over the parameter s (varied in small increments as was the parameter t), again looking for the value of s that minimizes the value of $D_{ij}$ (see FIG. 9). The procedure then reverts back to varying the parameter t while holding s at its previously determined value. In this process, the increments of t are taken to be somewhat smaller than the increments used in the first process. The procedure continues in this repeating fashion, making the increments successively smaller and smaller, until the value of $D_{ij}$ is less than a pre-determined small value denoted by the parameter $\epsilon$ in Procedure #3 illustrated in FIG. 7D. The value assigned to $\epsilon$ is chosen to establish the accuracy with which the common point of intersection is determined in this multi-step procedure. On the other hand, if when $D_{ij}$ is found not to change by an appreciable amount from one step to the next and its value is not very nearly zero, the two ambiguity circles in question are understood not to intersect.

Once common points of intersection for each pair of ambiguity circles have been found, vectors are formed for each point, each vector originating at the origin of the coordinate system and passing through the corresponding point of intersection of the two ambiguity circles. For an interferometer system consisting of n antennas, there are n−1 unique pairs giving rise to n−1 sets of ambiguity circles. The n−1 sets ambiguity circles give rise to no more than a total of ½ (n−1)(n−2) points of intersection and the same number of vectors; some circles of one set may not be well positioned to intersect with a particular circle of another set. For example six antennas give rise to five unique phase differences, and thus five sets of interferometer planes or five sets of ambiguity circles: thus no more than ten points of intersection.

A second method of finding the common point of intersection of two ambiguity circles relies upon projecting the two ambiguity circles onto the plane that contains the normal vectors of both interferometer planes. In this plane the two ambiguity circles are each reduced to straight lines and their common point of intersection is easily found using techniques familiar from high school algebra. The normal to this plane is found as the vector cross product of the normal vectors of the interferometer planes associated with the two ambiguity circles. The exact process is similar to the process described above: assign one of the two normal vectors to be the z'-axis unit vector for this new coordinate system; since this normal vector is already a unit vector no further normalization is required. Then assign the vector developed from the cross product of the two interferometer plane normal vectors to be the y'-axis unit vector of this new coordinate system once it has been properly normalized. Finally assign the cross product of this y'-axis unit vector with the z'-axis unit vector, specifically ŷ'×ẑ', to be the x'-axis unit vector once this vector too has been properly normalized.

In the next step, a coordinate system aligned with the second normal vector is developed exactly as described above using Equation 6 through Equation 13; this coordinate system will now be the double primed coordinate system. The parametric vector equation for the ambiguity circle associated with this second coordinate system is transformed to the primed coordinate system by first transforming it from the double primed coordinate system to the unprimed coordinate system and then, in turn, transforming it from the unprimed coordinate system to the primed coordinate system all in one step by a double matrix multiplication: to wit $$R_2'(s) = T_1^T \cdot T_2 \cdot R_2''(s). \quad (18)$$

The projection of $R_2'(s)$ onto the y'-z' plane is accomplished by forming the vector inner product of $R_2'(s)$ with a unit vector constructed from the unit vectors that parallel the y' and the z' axes. The point where this projection crosses the y' axis is the point where the two ambiguity circles intersect but in this primed coordinate system. Transforming this point back to the unprimed coordinate system produces the coordinates of the common point of intersection on the surface of the direction cosine sphere.

Once the common points of intersection for all possible combinations of the set of ambiguity circles have been found, it is possible to form direction vectors that extend from the unprimed coordinate system origin out through each point of intersection on the surface of the direction cosine sphere. It is noted that if all of these vectors are tightly grouped, the sum of the inner products is sure to be close to $(1/8)n^2(n-1)^2 - (1/4)n(n-1)$ where n is the number of direction vectors. On the other hand if one or more of these points are not contained within this group, the sum of the inner products is sure to be less than this number. The former case is illustrated in FIG. 10 and the latter in FIG. 11.

In one form, as noted above, the invention comprises a system for determining a direction of arrival of an rf signal emitted by a rf source. A first transducer (e.g., antenna A1) receives the emitted rf signal and provides a first transducer output signal corresponding to the emitted rf signal received by the first transducer. A second transducer (e.g., antenna A2) spaced a distance $D_{12}$ from the first transducer receives the emitted signal and provides a second transducer output signal corresponding to the emitted signal received by the second transducer. A first receiver (e.g., a channel of receiver 608) receives the first transducer output signal and provides a first receiver output signal indicating the phase of the first transducer output signal received by the first transducer. A second receiver (e.g., another channel of receiver 608) receives the second transducer output signal and provides a second receiver output signal indicating the phase of the second transducer output signal received by the second transducer. A processor (e.g., DSP 610) receives the first receiver output signal and the second receiver output signal and determines a first set of interferometer planes corresponding to a phase difference between the first transducer output signal and the second transducer output signal. The phase difference is a function of the distance $D_{12}$, and processor provides output information corresponding to a direction of arrival of the emitted signal relative to the first and second transducers. The output information is a function of an intersection of the set of interferometer planes with a direction cosine sphere.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A system for determining a direction of arrival of a signal emitted by a source and for resolving front to back phase ambiguity, said system comprising:
   a plurality of at least four non-collinear, non-coplanar, spaced transducers, each receiving the emitted signal and providing a transducer output signal corresponding to the received emitted signal;
   a multi-channel receiver, each channel associated with one of the transducers for receiving each associated transducer output signal and providing a receiver output signal indicating the phase of the received signal;
   a processor for receiving the receiver output signals and for processing the received transducer output signals by employing a direction finding algorithm to minimize phase ambiguities between the receiver output signals to determine a first direction and a second direction, said processor for determining an amplitude comparison between two of the received transducer output signals of the transducer elements and of the received transducer output signal of another transducer element receiving from a direction substantially opposite to a direction in which of the two transducers receive, and said processor selecting the first direction or the second direction as a function of the determined amplitude comparison, said selected direction corresponding to the direction of arrival of the emitted signal relative to the transducers.

2. The system of claim 1 wherein the transducers are antennas mounted on a surface of an aircraft.

3. The system of claim 1 wherein the transducers are selected from the following: antennas, rf sensors, sonaphones, sound sensors, seismic sensors, acoustic wave sensors and/or pressure sensors.

4. The system of claim 1 wherein:
   a first channel of the receiver receives a first transducer output signal and provides a first channel output signal having a phase corresponding to the phase of the signal received by a first transducer of the plurality of transducers;
   a second channel of the receiver receives the second transducer output signal and provides a second channel output signal having a phase corresponding to the phase of the signal received by a second transducer of the plurality of transducers; and the processor receives the first channel output signal and the second channel output signal and provides an output signal corresponding to the direction of arrival.

5. The system of claim 4 wherein the plurality of transducers comprises a first transducer and a second transducer and further comprising:
a third transducer receiving the emitted signal and providing a third transducer output signal corresponding to the emitted signal received by a third transducer of the plurality of transducers, said third transducer spaced a distance $D_{23}$ from the second transducer;
a third channel of the receiver for receiving the third transducer output signal and providing a third channel output signal indicating the phase of the third transducer output signal received by the third transducer; and
said processor receives the third channel output signal, said processor determining a set of interferometer planes corresponding to a phase difference between the second transducer output signal and the third transducer output signal, said phase difference being a function of the distance $D_{23}$, and said processor providing output information corresponding to a direction of arrival of the emitted signal relative to the first, second and third transducers, wherein the output information is a function of an intersection of the set of interferometer planes with a direction cosine sphere.

6. The system of claim 5 wherein said processor determines said amplitude comparison as a function of a distance $D_{23}$ between the second transducer and the third transducer.

7. The system of claim 6 wherein the transducers are antennas mounted on a surface of an aircraft.

8. The system of claim 1 wherein said processor determines said amplitude comparison as a function of a distance between two of said plurality of transducers.

9. A method for determining a direction of arrival of a signal emitted by a source and for resolving front to back phase ambiguity, said method comprising:
receiving the emitted signal via a plurality of at least four non-collinear, non-coplanar, spaced transducers, and providing a transducer output signal corresponding to the received emitted signal from each transducer;
receiving each associated transducer output signal and providing a receiver output signal indicating the phase of the received emitted signal;
processing the received transducer output signals by employing a direction finding algorithm to minimize phase ambiguities between the received transducer output signals to determine a first direction and a second direction;
determining an amplitude comparison between the received transducer output signals of two of the transducer elements and the received transducer output signal of another transducer element receiving from a direction substantially opposite to a direction in which of the two transducers receive;
selecting the first direction or the second direction as a function of the determined amplitude comparison, said selected direction corresponding to the direction of arrival of the emitted signal relative to the transducers.

10. The method of claim 9 wherein the transducers are antennas mounted on a surface of an aircraft.

11. The method of claim 9 wherein the transducers are selected from the following: antennas, rf sensors, sonaphones, sound sensors, seismic sensors, acoustic wave sensors and/or pressure sensors.

12. The method of claim 9 wherein receiving the emitted signal comprises receiving the emitted signal via a first transducer of the plurality of transducers and providing a first transducer output signal corresponding to the emitted signal received by the first transducer, and further comprising providing a first output signal having a phase corresponding to the phase of the received first transducer output signal; wherein receiving the emitted signal comprises receiving the emitted signal via a second transducer of the plurality of transducers and providing a second transducer output signal corresponding to the emitted signal received by the second transducer, and further comprising:
providing a second output signal having a phase corresponding to the phase of the second transducer output signal;
receiving the first output signal and the second output signal; and
providing an output signal corresponding to the direction of arrival.

13. The method of claim 12 wherein receiving the emitted signal comprises receiving the emitted signal via a third transducer of the plurality of transducers and providing a third transducer output signal corresponding to the emitted signal received by the third transducer; and further comprising
determining a second set of interferometer planes corresponding to a phase difference between the second transducer output signal and the third transducer output signal,
providing output information corresponding to a direction of arrival of the emitted signal relative to the first, second and third transducers, wherein the output information is a function of an intersection of the second set of interferometer planes with a second direction cosine sphere.

14. The method of claim 13 wherein said determining determines said amplitude comparison as a function of a distance $D_{23}$ between the second transducer and the third transducer.

15. The method of claim 14 wherein the transducers are antennas mounted on a surface of an aircraft.

16. The method of claim 9 wherein said determining determines said amplitude comparison as a function of a distance between two of said plurality of transducers.

* * * * *